(12) United States Patent
Kim et al.

(10) Patent No.: US 8,022,444 B2
(45) Date of Patent: Sep. 20, 2011

(54) BIOSENSOR AND METHOD OF MANUFACTURING THE SAME

(75) Inventors: Tae Youb Kim, Seoul (KR); Nae Man Park, Daejeon (KR); Han Young Yu, Daejeon (KR); Moon Gyu Jang, Daejeon (KR); Jong Heon Yang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 482 days.

(21) Appl. No.: 12/195,305

(22) Filed: Aug. 20, 2008

(65) Prior Publication Data

US 2009/0152597 A1  Jun. 18, 2009

(30) Foreign Application Priority Data

Dec. 17, 2007  (KR) .............................. 2007-132758

(51) Int. Cl.
*H01L 27/085* (2006.01)
*H01L 27/14* (2006.01)
*H01L 21/00* (2006.01)

(52) U.S. Cl. ............... 257/255; 257/414; 257/E21.002; 257/E51.038; 257/E51.04; 257/E31.002; 257/E31.003; 438/795; 438/796; 438/797; 438/798; 438/799; 977/710; 977/742; 977/963

(58) Field of Classification Search ................. 257/255, 257/414, E21.002, E51.038, E51.04, E31.002, 257/E31.003; 438/795, 796, 797, 798, 799; 977/710, 742, 963

See application file for complete search history.

(56) References Cited

U.S. PATENT DOCUMENTS 6,870,235 B2  3/2005  Abstreiter et al.
2009/0140167 A1*  6/2009  Ward et al. ................. 250/458.1

FOREIGN PATENT DOCUMENTS

KR  1020060036487 A  4/2006

OTHER PUBLICATIONS

Eric Stern et al., "Label-free immunodetection with CMOS-compatible semiconductor nanowires", Nature vol. 445, Feb. 2007, Nature Publishing Group, pp. 519-522.
Yi Cui et al., "Nanowire Nanosensors for Highly Sensitive and Selective Detection of Biological and Chemical Species", Science, Aug. 17, 2001, vol. 293, pp. 1289-1292.
Gengfeng Zheng et al., "Multiplexed electrical detection of cancer markers with nanowire sensor arrays", Nature Biotechnology, Oct. 10, 2005, vol. 23 No. 10, pp. 1294-1301.

* cited by examiner

*Primary Examiner* — Long K Tran

(57) ABSTRACT

Provided are a biosensor with a silicon nanowire and a method of manufacturing the same, and more particularly, a biosensor with a silicon nanowire including a defect region formed by irradiation of an electron beam, and a method of manufacturing the same. The biosensor includes: a silicon substrate; a source region disposed on the silicon substrate; a drain region disposed on the silicon substrate; and a silicon nanowire disposed on the source region and the drain region, and having a defect region formed by irradiation of an electron beam. Therefore, by irradiating a certain region of a high-concentration doped silicon nanowire with an electron beam to lower electron mobility in the certain region, it is possible to maintain a low contact resistance between the silicon nanowire and a metal electrode and to lower operation current of a biomaterial detection part, thereby improving sensitivity of the biosensor.

7 Claims, 4 Drawing Sheets

BIOSENSOR AND METHOD OF MANUFACTURING THE SAME

CROSS-REFERENCE TO RELATED APPLICATION

This application claims the benefit of Korean Patent Application No. 2007-132758, filed Dec. 17, 2007, the disclosure of which is hereby incorporated herein by reference in its entirety.

BACKGROUND

1. Field of the Invention

The present invention relates to a biosensor with a silicon nanowire and a method of manufacturing the same, and more particularly, to a biosensor with a silicon nanowire including a defect region formed by irradiation of an electron beam, and a method of manufacturing the same.

This work was supported by the IT R&D program of MIC/IITA. [2006-S-007-02, Ubiquitous Health Monitoring Module and System Development].

2. Discussion of Related Art

In general, a biosensor is a device for measuring variation depending on biochemical, optical, thermal, or electrical reaction. The latest tendency in research has been toward research on electrochemical biosensors.

The electrochemical biosensor senses variations of conductivity generated from reactions between a target molecule and a probe molecule in a silicon nanowire to detect a specific biomaterial.

FIG. 1 illustrates a structure of a conventional biosensor.

Referring to FIG. 1, the conventional biosensor includes a silicon substrate 100, source and drain regions 110 and 120 formed on the silicon substrate 100, and an insulating layer 130 disposed between the source and drain regions 110 and 120, according to a basic structure of a field effect transistor (FET). A pre-manufactured silicon nanowire 140 is dispersed on the source and drain regions 110 and 120, and the insulating layer 130. Then, after finding the silicon nanowire that is capable of connecting the source and drain regions 110 and 120 by means of an electron microscope, metal electrodes 150 are patterned to make the silicon nanowire 140 in contact with the source and drain regions 110 and 120.

At this time, in order to improve performance of the transistor, the doping concentration of the silicon nanowire must be increased to improve electron mobility, thereby lowering contact resistance against the metal electrodes. On the other hand, in order to increase sensitivity of the biosensor, the doping concentration of the silicon nanowire must be lowered to decrease electron mobility such that the silicon nanowire is operated at a low current. This is because the difference in surface charge when a biomaterial adheres to a nanowire surface can be more effectively detected when a current flowing through the silicon nanowire is lowered.

Therefore, in order to improve performance and sensitivity of the biosensor manufactured on the basis of the transistor structure, it is necessary to provide a biosensor manufacturing method capable of lowering contact resistance between the silicon nanowire and the metal electrodes and lowering current flowing through the silicon nanowire.

SUMMARY OF THE INVENTION

The present invention is directed to a biosensor having good transistor performance and high sensitivity, and a method of manufacturing the same.

One aspect of the present invention provides a biosensor including: a silicon substrate; a source region disposed on the silicon substrate; a drain region disposed on the silicon substrate; and a silicon nanowire disposed on the source region and the drain region, and having a defect region formed by irradiation of an electron beam.

Another aspect of the present invention provides a method of manufacturing a biosensor, including: providing a silicon substrate; forming a source region and a drain region on the silicon substrate; disposing a silicon nanowire on the source region and the drain region; and irradiating an electron beam to a predetermined region of the silicon nanowire to form a defect region.

BRIEF DESCRIPTION OF THE DRAWINGS

The above and other features of the present invention will be described in reference to certain exemplary embodiments thereof with reference to the attached drawings in which.

DETAILED DESCRIPTION OF PREFERRED EMBODIMENTS

Figure 1:
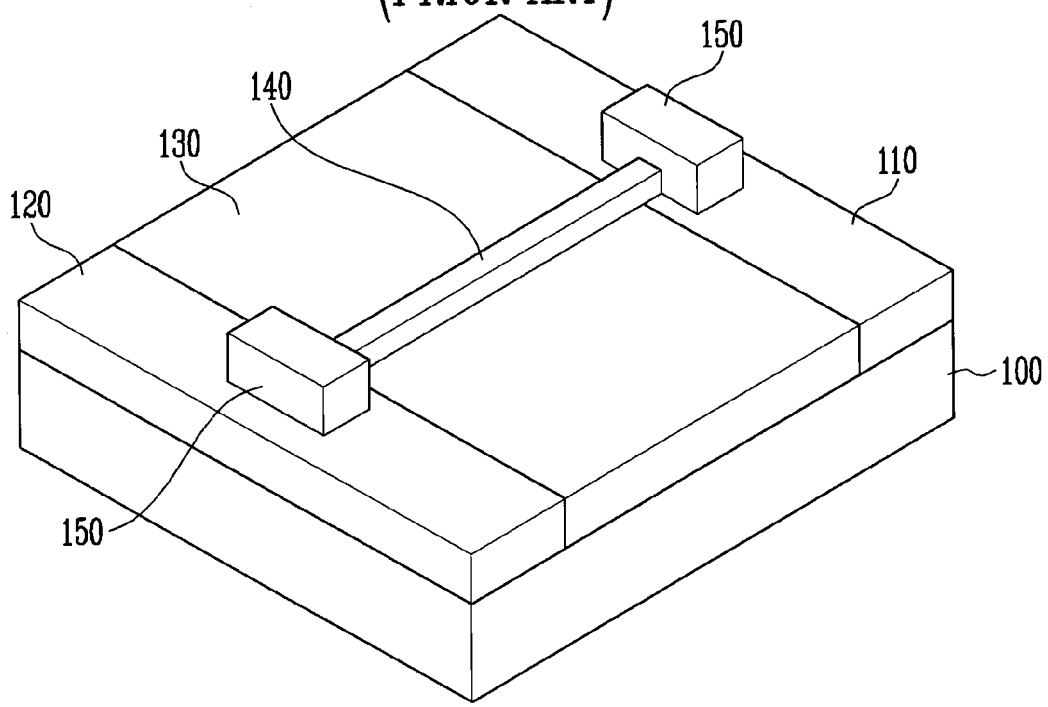
FIG. 1 illustrates a structure of a conventional biosensor.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the following description, when it is mentioned that a layer is disposed "on" another layer or a substrate, it means that the layer may be directly formed on the other layer or a third layer may be interposed therebetween. In the drawings, the thickness of layers and regions are exaggerated for clarity. Like reference numerals designate like elements throughout the specification.

Figure 2:
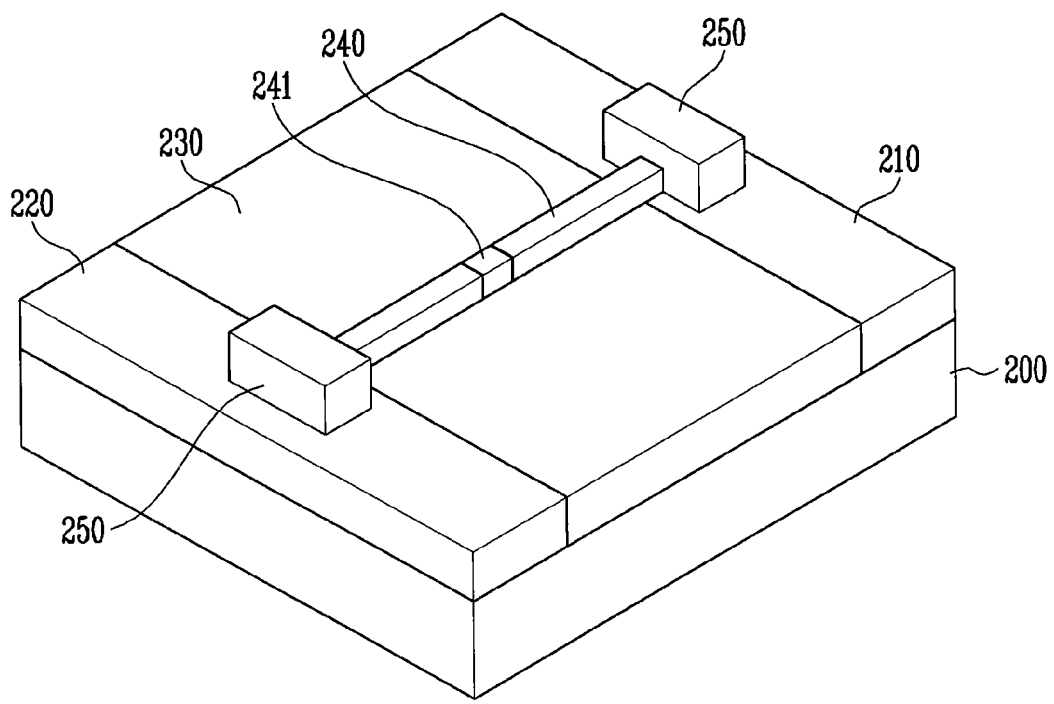
FIG. 2 illustrates configuration of a biosensor according to an exemplary embodiment of the present invention.

FIG. 2 illustrates configuration of a biosensor according to an exemplary embodiment of the present invention.

Referring to FIG. 2, the biosensor according to an exemplary embodiment of the present invention includes a source region 210 and a drain region 220, which are formed on a silicon substrate 200 doped with a high concentration. Here, when the silicon substrate 200 is doped with a p-type impurity, the source region 210 and the drain region 220 are doped with an n-type impurity, and when the silicon substrate 200 is doped with an n-type impurity, the source region 210 and the drain region 220 are doped with a p-type impurity.

An insulating layer 230 is disposed between the source region 210 and the drain region 220, and a silicon nanowire 240 connecting the source region 210 to the drain region 220 is disposed on the source region 210, the drain region 220, and the insulating layer 230. The silicon nanowire 240 is electrically connected to the source region 210 and the drain region 220 by patterned metal electrodes 250. At this time, the doping concentration of the silicon nanowire 240 is $10^{18}/cm^3$ or more (preferably, $10^{18}/cm^3$ to $10^{21}/cm^3$).

Meanwhile, the silicon nanowire 240 includes a defect region 241 formed by irradiation of an electron beam, different from the silicon nanowire included in the conventional biosensor. In an exemplary embodiment, the length of the defect region 241 is within a range of 5 nm to 100 nm.

The defect region 241 formed by irradiation of an electron beam remarkably decreases electron mobility such that low current operation characteristics required to manufacture a high sensitive biosensor can be satisfied. Therefore, the biosensor according to the present invention can effectively sense a biomaterial attached to the defect region 241.

In addition, since regions of the silicon nanowire other than the defect region 241 still have high electron mobility, a contact resistance generated with the source region 210 or the drain region 220 can be lowered. In an exemplary embodiment, a difference in electron mobility between the defect region 241 and the other regions is $1/5$ or more of the electron mobility of the other regions.

FIGS. 3A to 3D illustrate a method of manufacturing a biosensor according to an exemplary embodiment of the present invention.

Figure 3A:
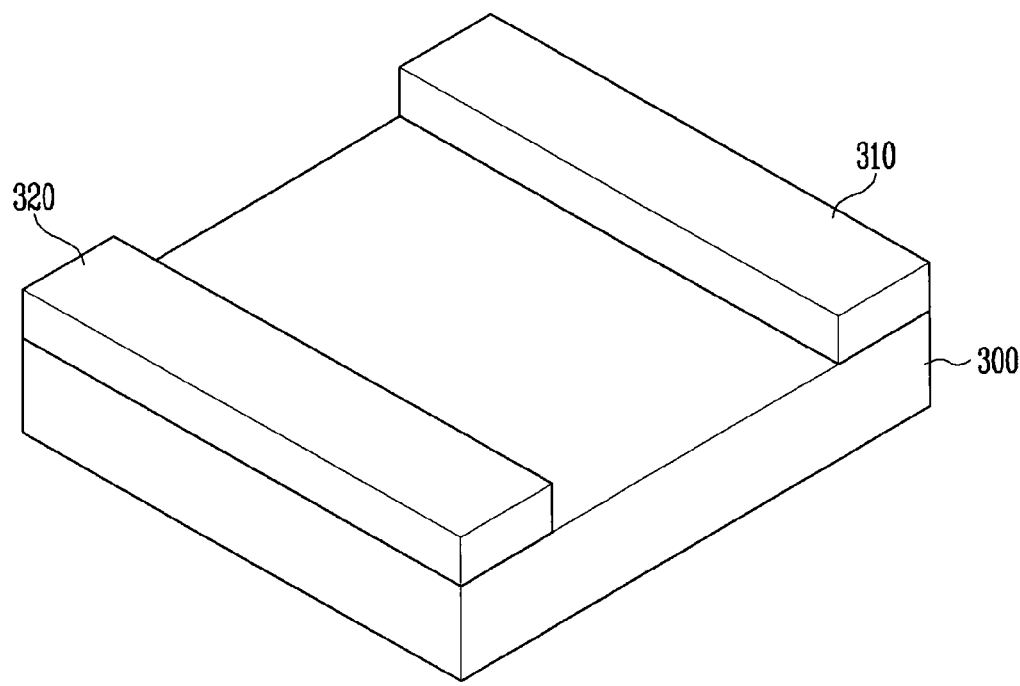
FIGS. 3A to 3D illustrate a method of manufacturing a biosensor according to an exemplary embodiment of the present invention.

Referring to FIG. 3A, a source region 310 and a drain region 320 are formed on a silicon substrate 300. In an exemplary embodiment, the silicon substrate 300 may be formed of a silicon on insulator (SOI) substrate. When the silicon substrate 300 is doped with a p-type impurity, the source region 310 and the drain region 320 are doped with an n-type impurity using phosphorus (P), and when the silicon substrate 300 is doped with an n-type impurity, the source region 310 and the drain region 320 are doped with a p-type impurity using boron (B).

Figure 3B:
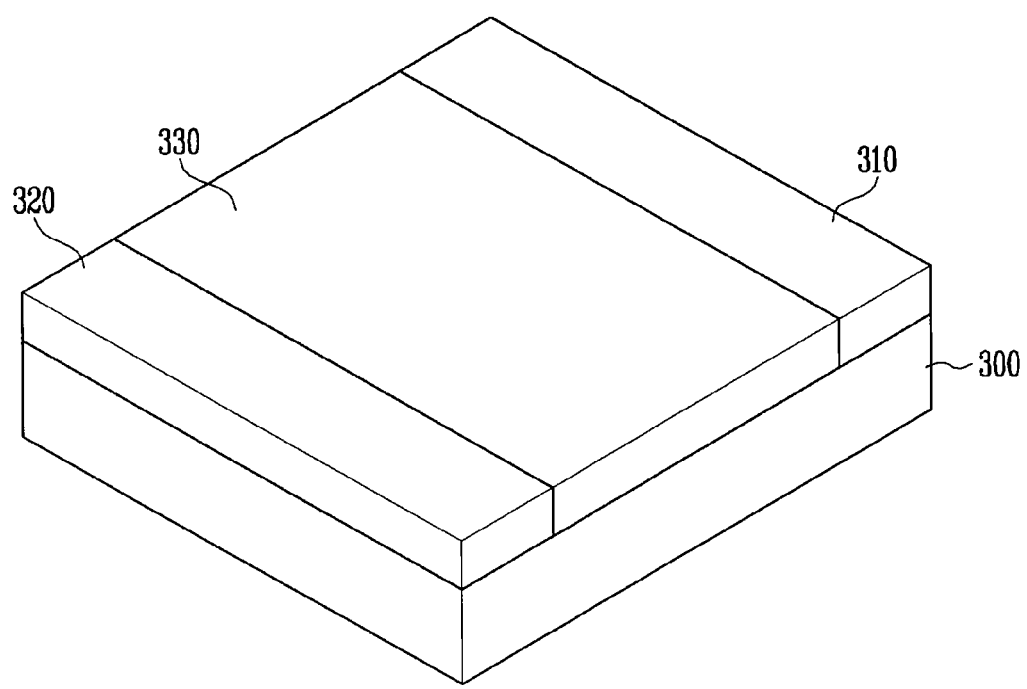

Referring to FIG. 3B, an insulating layer 330 is formed between the source region 310 and the drain region 320 on the silicon substrate 300. In an exemplary embodiment, the insulating layer 330 may be formed by depositing a silicon oxide layer or a silicon nitride layer using a chemical vapor deposition (CVD) or physical vapor deposition (PVD) method. In addition, when the silicon substrate 300 is the SOI substrate, a step of forming the insulating layer 330 may be omitted.

Figure 3C:
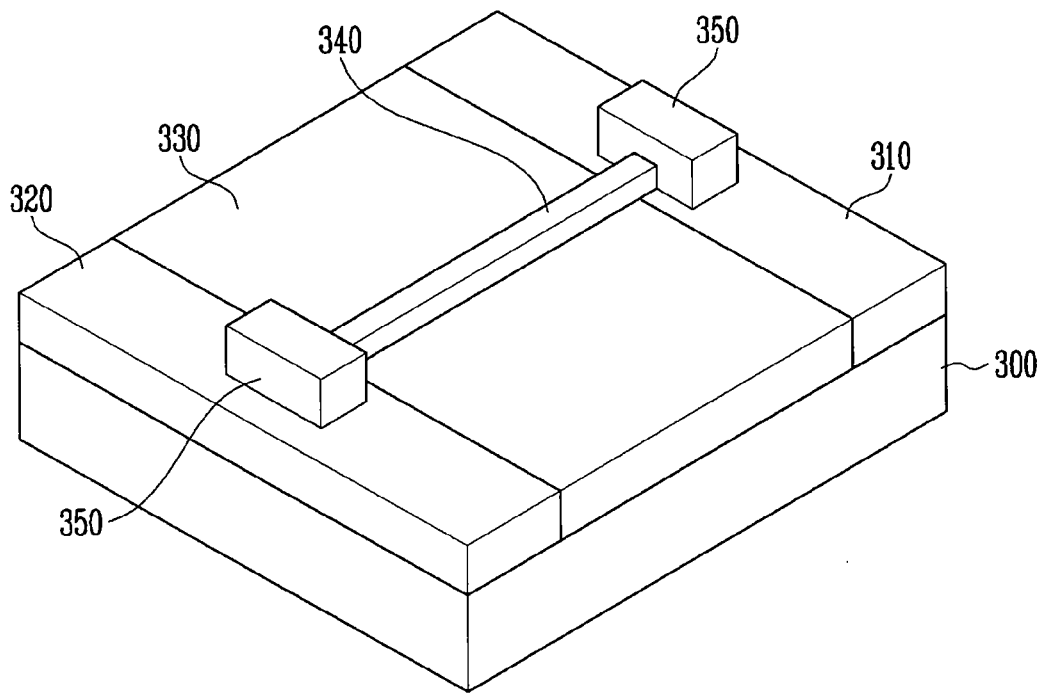

Referring to FIG. 3C, a silicon nanowire 340 is disposed on the source region 310, the drain region 320, and the insulating layer 330. A pre-manufactured silicon nanowire 340 is dispersed on the source and drain regions 310 and 320, and the insulating layer 330. Then, metal electrodes 350 are patterned to make the silicon nanowire 340 in contact with the source and drain regions 310 and 320 after finding a silicon nanowire capable of connecting the source and drain regions 310 and 320 using an electron microscope. In an exemplary embodiment, the metal electrodes 350 may be formed of gold or aluminum, and may be patterned by depositing a metal material through sputtering and etching the metal material.

Figure 3D:
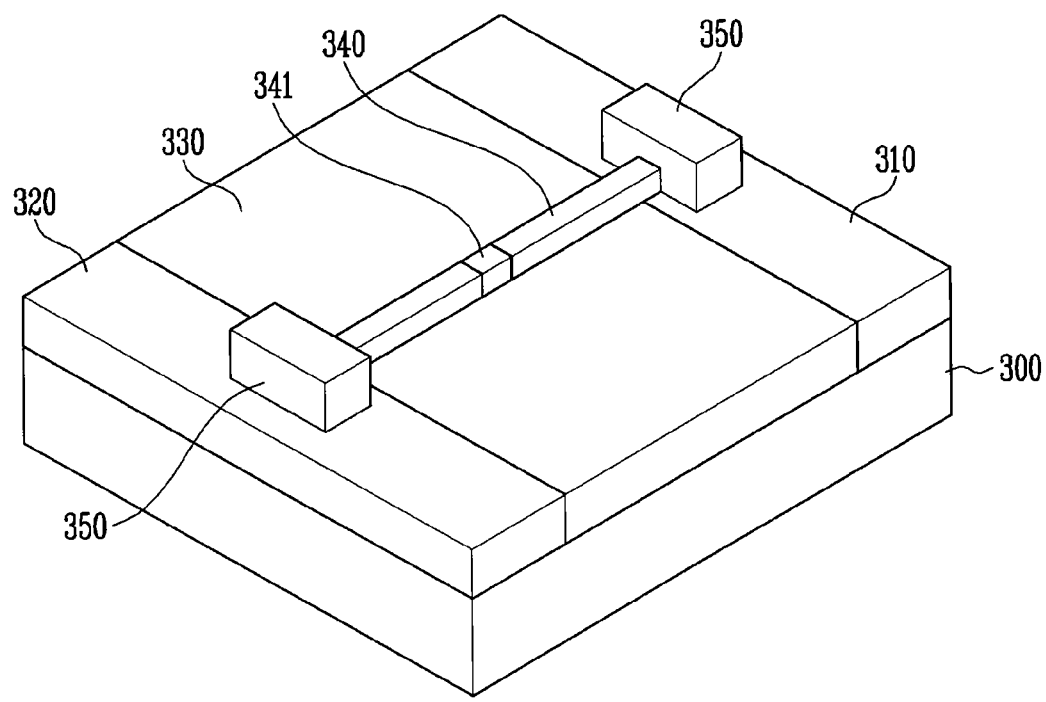

Referring to FIG. 3D, an electron beam is irradiated to one region of the silicon nanowire 340 to form a defect region 341. At this time, the defect region 341 may be formed by irradiating an electron beam with an accelerated voltage of 100 keV or more (preferably, 100 keV to 300 keV) using a scanning electron microscope (SEM), and so on, and the defect region 341 may have a length of 5 nm to 100 nm.

Figure 4:
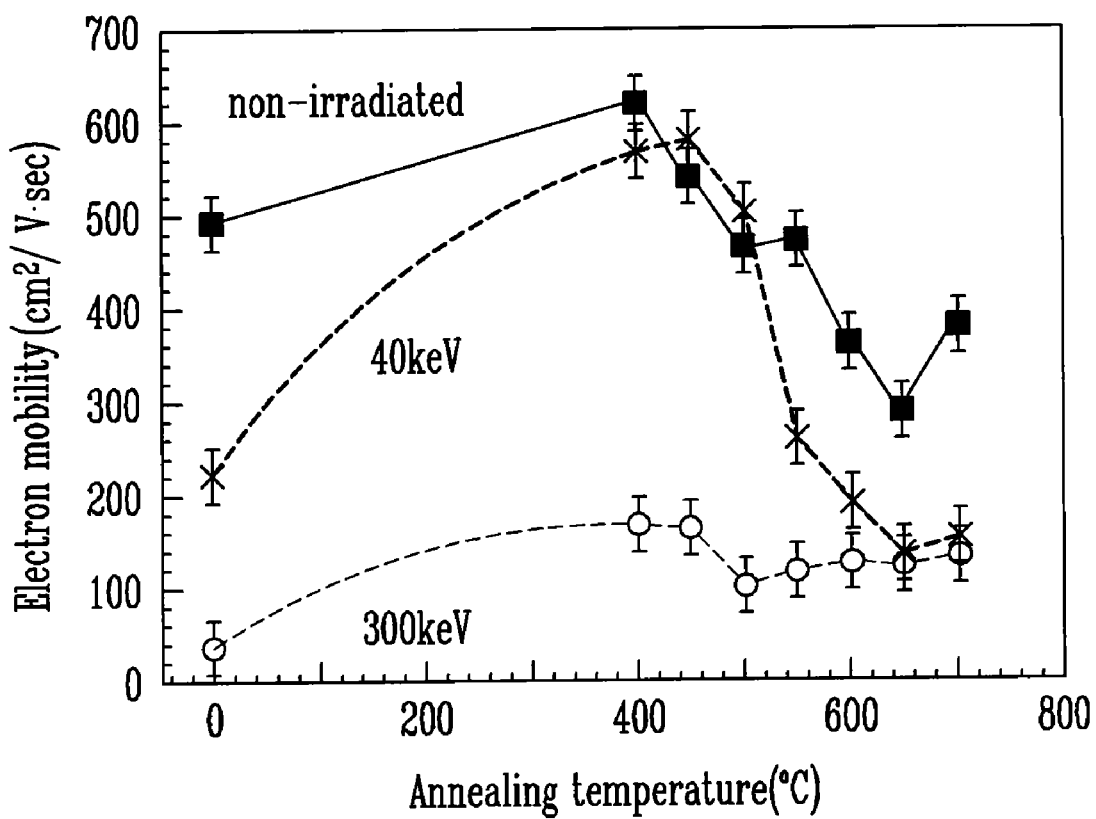
FIG. 4 is a graph showing electron mobility characteristics of a silicon nanowire included in a biosensor manufactured according to the present invention.

FIG. 4 is a graph showing electron mobility characteristics of a silicon nanowire included in a biosensor manufactured according to the present invention.

Referring to FIG. 4, the graph shows electron mobility of the silicon nanowire formed of a SiGe material including silicon 87% according to an amount of the irradiated electron beam.

Before post-annealing, the electron mobility of the silicon nanowire irradiated with an electron beam of 300 keV is lowered to $1/10$ or less of that of the silicon nanowire on which an electron beam is not irradiated. After post-annealing, the electron mobility of the silicon nanowire irradiated with an electron beam of 300 keV is lowered to about $1/6$ of that of the silicon nanowire on which an electron beam is not irradiated. In addition, before the post-annealing, the electron mobility of the silicon nanowire irradiated with an electron beam of 40 keV is lowered to $1/2$ or less of that of the silicon nanowire on which an electron beam is not irradiated. After the post-annealing, the electron mobility of the silicon nanowire irradiated with an electron beam of 40 keV is lowered to about $1/5$ of that of the silicon nanowire on which an electron beam is not irradiated. Therefore, the electron mobility of the defect region of the silicon nanowire can be effectively reduced through irradiation of the electron beam, and both transistor performance and sensitivity of the biosensor can be improved according to the above structure.

As can be seen from the foregoing, by irradiating a certain region of a high-concentration doped silicon nanowire with an electron beam to lower electron mobility in the certain region, it is possible to maintain a low contact resistance between the silicon nanowire and a metal electrode and to lower operation current of a biomaterial detection part, thereby improving sensitivity of a biosensor.

Although the present invention has been described with reference to certain exemplary embodiments thereof, it will be understood by those skilled in the art that a variety of modifications and variations may be made to the present invention without departing from the spirit or scope of the present invention defined in the appended claims, and their equivalents.

What is claimed is:

1. A biosensor comprising:
a silicon substrate;
a source region disposed on the silicon substrate;
a drain region disposed on the silicon substrate;
a silicon nanowire disposed on the source region and the drain region, and having a defect region formed by irradiation of an electron beam; and
wherein the defect region has a lower electron mobility than other regions of the silicon nanowire.

2. The biosensor according to claim 1, further comprising an insulating layer disposed between the source region and the drain region on the silicon substrate,
wherein the silicon nanowire is disposed on the source region, the drain region and the insulating layer.

3. The biosensor according to claim 1, further comprising:
a first electrode disposed on the source region and electrically connecting the source region to the silicon nanowire; and
a second electrode disposed on the drain region and electrically connecting the drain region to the silicon nanowire.

4. The biosensor according to claim 1, wherein the silicon nanowire has a doping concentration of $10^{18}/cm^3$ to $10^{21}/cm^3$.

5. The biosensor according to claim 1, wherein the defect region has a length of 5 nm to 100 nm.

6. The biosensor according to claim 1, wherein the defect region is formed by an electron beam irradiated with an accelerated voltage of 100 keV to 300 keV.

7. The biosensor according to claim 1, wherein the silicon substrate is formed of a silicon on insulator (SOI) substrate.

* * * * *